United States Patent [19]

North et al.

[11] Patent Number: 4,985,422

[45] Date of Patent: Jan. 15, 1991

[54] LACTAM DERIVATIVES

[75] Inventors: Peter C. North; Alexander W. Oxford, both of Royston; Ian H. Coates, Hertford; Paul J. Beswick, Ware, all of England

[73] Assignee: Glaxo Group Limited, England

[21] Appl. No.: 343,359

[22] Filed: Apr. 26, 1989

[30] Foreign Application Priority Data

Apr. 27, 1988 [GB] United Kingdom ............... 8809933
Sep. 1, 1988 [GB] United Kingdom ............... 8820652
Sep. 1, 1988 [GB] United Kingdom ............... 8820648

[51] Int. Cl.$^5$ ............... C07D 487/04; C07D 471/04; A61K 31/55; A61K 31/445
[52] U.S. Cl. ............................ 514/215; 540/521; 546/86; 546/89; 546/80; 546/92; 514/291; 514/292
[58] Field of Search ............. 540/521; 514/215, 291, 514/292; 546/86, 89, 92, 80

[56] References Cited

U.S. PATENT DOCUMENTS

| | | | |
|---|---|---|---|
| 3,563,979 | 2/1971 | Hester | 540/521 |
| 4,695,578 | 9/1987 | Coates et al. | 514/397 |
| 4,725,615 | 2/1988 | Coates et al. | 514/397 |
| 4,749,718 | 6/1988 | Coates et al. | 514/397 |
| 4,808,581 | 2/1989 | Oxford et al. | 514/212 |
| 4,822,881 | 4/1989 | Coates et al. | 540/603 |
| 4,859,662 | 8/1989 | Coates et al. | 514/212 |

FOREIGN PATENT DOCUMENTS 2400518 3/1979 France .
39-20857 9/1964 Japan ............................. 546/86

OTHER PUBLICATIONS

March, J., *Advanced Organic Chemistry*, McGraw Hill, New York, NY 1968, p. 331.

*Primary Examiner*—Mary C. Lee
*Assistant Examiner*—Lenora Miltenberger
*Attorney, Agent, or Firm*—Bacon & Thomas

[57] ABSTRACT

Compounds which are potent and selective antagonists of the effect of 5-HT$_3$ receptors and are useful in the treatment of psychotic disorders, anxiety, and nausea and vomiting, of the general formula (I)

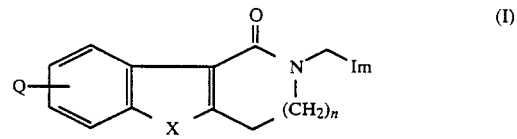

wherein Im represents an imidazolyl group of the formula (a), (b) or (c):

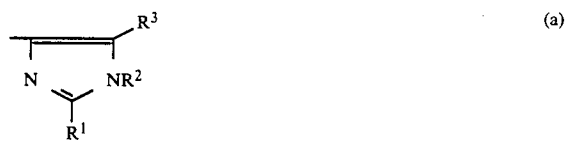

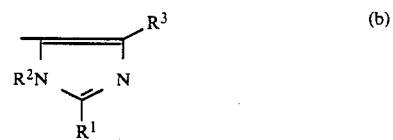

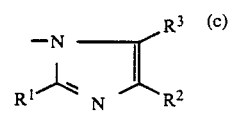

one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkyl group;
n represents 1 or 2;
Q represents a hydrogen atom, a halogen atom, or a hydroxy, $C_{1-4}$alkoxy, phenyl $C_{1-3}$alkoxy or $C_{1-6}$alkyl group, or a group —$NR^4R^5$ or —$CONR^4R^5$; and
X represents an oxygen or a sulphur atom, and, when Im represents an imidazolyl group of formula (c), X may also represent the group $NR^6$, where $R^6$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alklyl, —$CO_2R^7$, —$COR^7$, —$CONR^7R^8$ or —$SO_2R^7$; and physiologically acceptable salts or solvates thereof.

11 Claims, No Drawings

LACTAM DERIVATIVES

This invention relates to lactam derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at 5-HT$_3$ receptors have been described previously.

Thus for example published UK patent specification No. 2153821A and published European patent specification Nos. 191562, 219193 and 210840 disclose 3-imidazolylmethyltetrahydrocarbazolones which may be represented by the general formula:

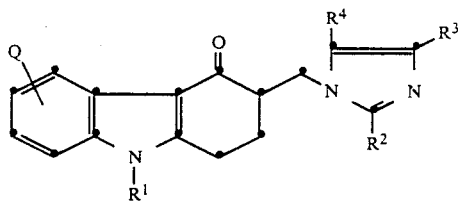

wherein R$^1$ represents a hydrogen atom or a group selected from C$_{1-10}$alkyl, C$_{3-6}$alkenyl, C$_{3-10}$alkynyl, C$_{3-7}$cycloalkyl, C$_{3-7}$cycloalkylC$_{1-4}$alkyl, phenyl or phenylC$_{1-3}$alkyl, and in the case where Q represents a hydrogen atom, R$^1$ may also represent —CO$_2$R$^5$, —COR$^5$, —CONR$^5$R$^6$ or —SO$_2$R$^5$ (wherein R$^5$ and R$^6$, which may be the same or different, each represents a hydrogen atom, a C$_{1-6}$alkyl or C$_{3-7}$cycloalkyl group, or a phenyl or phenylC$_{1-4}$alkyl group, in which the phenyl group is optionally substituted by one or more C$_{1-4}$alkyl, C$_{1-4}$alkoxy or hydroxy groups or halogen atoms, with the proviso that R$^5$ does not represent a hydrogen atom when R$^1$ represents a group —CO$_2$R$^5$ or —SO$_2$R$^5$); one of the groups represented by R$^2$, R$^3$ and R$^4$ is a hydrogen atom or a C$_{1-6}$alkyl, C$_{3-7}$cycloalkyl, C$_{2-6}$alkenyl, or phenylC$_{1-3}$alkyl group, and each of the other two groups, which may be the same or different, represents a hydrogen atom or a C$_{1-6}$alkyl group; Q represents a hydrogen atom or a halogen atom or a hydroxy, C$_{1-4}$alkoxy, phenylC$_{1-3}$alkoxy or C$_{1-6}$alkyl group or a group —NR$^7$R$^8$ or —CONR$^7$R$^8$ (wherein R$^7$ and R$^8$, which may be the same or different, each represents a hydrogen atom or a C$_{1-4}$alkyl or C$_{3-4}$alkenyl group, or together with the nitrogen atom to which they are attached form a saturated 5 to 7 membered ring); and physiologically acceptable salts and solvates thereof.

Furthermore, published European patent specification No. 242973 discloses ketone derivatives which may be represented by the general formula:

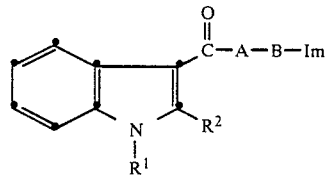

wherein Im represents an imidazolyl group of formula:

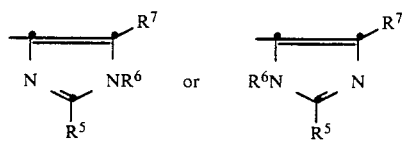

R$^1$ represents a hydrogen atom or a C$_{1-6}$alkyl, C$_{3-6}$alkenyl, C$_{3-10}$alkynyl, C$_{3-7}$cycloalkyl, C$_{3-7}$cycloalkylC$_{1-4}$alkyl, phenyl or phenylC$_{1-3}$alkyl group;

R2 represents a hydrogen atom or a C$_{1-6}$alkyl, C$_{3-6}$alkenyl, C$_{3-7}$cycloalkyl, phenyl or phenylC$_{1-3}$alkyl group;

A—B represents the group R$^3$R$^4$C—CH$_2$ or R$^3$C=CH;

R$^3$ and R$^4$, which may be the same or different, each represents a hydrogen atom or a C$_{1-6}$alkyl group;

one of the groups represented by R$^5$, R$^6$ and R$^7$, is a hydrogen atom or a C$_{1-6}$alkyl, C$_{3-7}$cycloalkyl, C$_{3-6}$alkenyl, phenyl or phenylC$_{1-3}$alkyl group, and each of the other two groups, which may be the same or different, represents a hydrogen atom or a C$_{1-6}$alkyl group; and physiologically acceptable salts and solvates thereof.

We have now found a novel group of compounds which differ in structure from those described previously, and which are potent antagonists of the effect of 5-HT at 5-HT$_3$ receptors.

Thus the present invention provides a tricyclic lactam of the general formula (I):

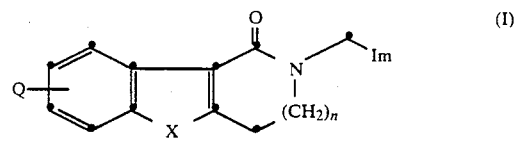

wherein Im represents an imidazolyl group of the formula (a), (b) or (c):

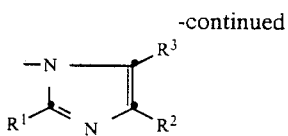

and one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

n represents 1 or 2;

Q represents a hydrogen atom, a halogen atom, or a hydroxy, $C_{1-4}$-alkoxy, phenyl$C_{1-3}$alkoxy or $C_{1-6}$ alkyl group, or a group —$NR^4R^5$ or —$CONR^4R^5$ (wherein $R^4$ and $R^5$, which may be the same or different, each represents a hydrogen atom or a $C_{1-4}$alkyl or $C_{3-4}$alkenyl group, or together with the nitrogen atom to which they are attached form a saturated 5 to 7 membered ring);

and X represents an oxygen or a sulphur atom, and, when Im represents an imidazolyl group of formula (c), X may also represent the group $NR^6$, wherein $R^6$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, —$CO_2R^7$, —$COR^7$, —$CONR^7R^8$ or —$SO_2R^7$ (wherein $R^7$ and $R^8$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^7$ does not represent a hydrogen atom when $R^6$ represents a group —$CO_2R^7$ or —$SO_2R^7$);

and physiologically acceptable salts and solvates thereof.

According to one aspect, the invention provides compounds of formula (I) wherein X represents an oxygen or a sulphur atom, Q represents a hydrogen atom, and Im represents an imidazolyl group of formula (a) or (b) ($R^1$, $R^2$, $R^3$ and n being as defined in formula (I)).

According to another aspect, the invention provides compounds of formula (I) wherein X represents the group $NR^6$ and Im represents an imidazolyl group of formula (c) ($R^1$, $R^2$, $R^3$, $R^6$, Q and n being as defined in formula (I)).

According to another aspect, the invention provides compounds of formula (I) wherein X represents an oxygen or a sulphur atom and Im represents an imidazolyl group of formula (c) ($R^1$, $R^2$, $R^3$, Q and n being as defined in formula (I)).

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, n-propyl, prop-2-yl, n-butyl, but-2-yl, 2-methylprop-2-yl, n-pentyl, pent-3-yl or n-hexyl. A $C_{3-6}$alkenyl group may be, for example, a propenyl or butenyl group. When $R^6$ represents a $C_{3-6}$alkenyl or $C_{3-10}$alkynyl group, or Im represents an imidazolyl group of formula (a) or (b) and $R^2$ represents a $C_{3-6}$alkenyl group, or $R^4$ or $R^5$ represents a $C_{3-4}$alkenyl group, the double or triple bond may not be adjacent to the nitrogen atom. A phenyl$C_{1-3}$alkyl group may be, for example, a benzyl, phenethyl or 3-phenylpropyl group. A $C_{3-7}$cycloalkyl group may be, for example, a cyclopropyl, cyclobutyl, cyclopentyl, cyclohexyl or cycloheptyl group. A $C_{1-4}$alkoxy group may be, for example, a methoxy group. A halogen atom may be, for example, a fluorine, chlorine or bromine atom.

The substituent Q may be at any position in the benzenoid ring.

A preferred class of compounds of formula (I) is that in which Im represents an imidazolyl group of formula (a) or (b).

Another preferred class of compounds of formula (I) is that in which $R^1$, $R^2$ and $R^3$ each independently represents a hydrogen atom or a $C_{1-6}$alkyl group, more particularly a hydrogen atom or a $C_{1-3}$alkyl (e.g. methyl) group.

A further preferred class of compounds of formula (I) is that in which Im represents an imidazolyl group of formula (a) or (b), and $R^1$ and $R^2$ each represent a hydrogen atom and $R^3$ represents a $C_{1-3}$alkyl (e.g. methyl) group.

Another preferred class of compounds of formula (I) is that in which Im represents an imidazolyl group of formula (c), and $R^1$ represents a $C_{1-3}$alkyl (e.g. methyl) group, and $R^2$ and $R^3$ each represent a hydrogen atom.

Another preferred class of compounds of formula (I) is that in which n represents 1.

A further preferred class of compounds of formula (I) is that in which Q represents a hydrogen atom.

A further preferred class of compounds of formula (I) is that in which X represents an oxygen or a sulphur atom or a group $NR^6$ wherein $R^6$ represents a $C_{1-3}$alkyl (e.g. methyl) group.

A preferred group of compounds of formula (I) is that in which $R^1$, $R^2$ and $R^3$ each represent a hydrogen atom or a $C_{1-3}$alkyl (e.g. methyl) group, n represents 1, Q represents a hydrogen atom and X represents an oxygen or sulphur atom or the group $NR^6$ where $R^6$ represents a $C_{1-3}$alkyl (e.g. methyl) group.

Within the above preferred group of compounds, a particularly preferred group of compounds are those in which Im represents an imidazolyl group of formula (a) or (b).

Preferred compounds of the invention are 3,4-dihydro-2-[(5-methyl-1H-imidazol-4-yl)methyl]-benzofuro[3,2-c]pyridin-1(2H)-one and 3,4-dihydro-2-[(5-methyl-1H-imidazol-4-yl)methyl]-[1]-benzothieno-[3,2-c]pyridin-1(2H)-one, and their physiologically acceptable salts and solvates.

The potent and selective antagonism of 5-HT at 5-HT$_3$ receptors by compounds of the invention has been demonstrated by their ability to inhibit 3-(5-methyl-1H-imidazol-4-yl)-1-[1-(methyl-t$_3$)-1H-indol-3yl]-1-propanone binding in rat entorhinal cortex homogenates (following the general procedure described by G. Kilpatrick et al. in *Nature*, 1987, 330, 746), and/or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; pain; dependency on drugs and substances of abuse; depression; or dementia or another cognitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine H$_2$-receptor antagonists (e.g. ranitidine, sufotidine, 1-methyl-5-[[3-[3-(1-piperidinylmethyl)phenoxy]propyl]amino]-1H-1,2,4-triazole-3-methanol, cimetidine, famotidine, nizatidine or roxatidine) or H$^+$K$^+$ATPase inhibitors (e.g. omeprazole). In the treatment of nausea and vomiting, compounds of formula (I) may also be administered in combination with dexamethasone.

A proposed dose of the compounds of the invention for administration to man (of approximately 70 kg body weight) is 0.001 to 100 mg, preferably 0.01 to 50 mg, more preferably 0.1 to 20 mg of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1, R^2, R^3, R^6, n, Q$ and Im are as defined for compounds of general formula (I) unless otherwise stated.

According to first general process (A), a compound of general formula (I) may be prepared by reacting a compound of formula (II):

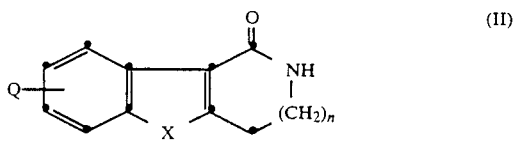

wherein X represents an oxygen or a sulphur atom or the group $NR^6$, or a protected derivative thereof, with a compound of formula (III):

or a salt of protected derivative thereof, wherein L represents a leaving atom or group such as a halogen atom (e.g. chlorine, bromine or iodine), an acyloxy group (e.g. trifluoroacetyloxy or acetoxy), or a sulphonyloxy group (e.g. trifluoromethanesulphonyloxy, p-toluenesulphonyloxy or methanesulphonyloxy), and Im represents an imidazolyl group of formula (a), (b) or (c), with the proviso that Im is a group of formula (c) when the compound of formula (III) is reacted with a compound of formula (II) wherein X represents the group $NR^6$, in the presence of a base, followed where necessary by removal of any protecting groups.

Suitable bases include alkali metal hydrides (e.g. sodium hydride), alkali metal carbonates (e.g. sodium carbonate), alkali metal amides (e.g. sodium amide or lithium diisopropylamide), alkali metal alkoxides (e.g. potassium t-butoxide) or alkali metal hydroxides (e.g. sodium or potassium hydroxide). The reaction may conveniently be carried out in an inert solvent such as an ether (e.g. dimethoxyethane, diglyme or tetrahydrofuran), a substituted amide (e.g. dimethylformamide or N-methylpyrrolidone), an aromatic hydrocarbon (e.g. toluene), a ketone (e.g. acetone) or dimethyl sulphoxide, and at a temperature of $-80°$ to $+100°$ C., preferably $-80°$ to $+50°$ C.

According to another general process (B), a compound of general formula (I) may be converted into another compound of formula (I) using conventional techniques. Such conventional techniques include hydrogenation, alkylation, acylation and acid-catalysed cleavage using protection and deprotection where necessary.

Thus, according to one embodiment of the interconversion process (B), hydrogenation may be used to convert an alkenyl or an alkynyl substituent into an alkyl substituent, or an alkynyl into an alkenyl substituent, or a benzyloxy substituent into a hydroxyl group. Hydrogenation according to general process (B) may be effected using conventional procedures, for example, using hydrogen in the presence of a catalyst, as described in published European patent specification No. 242973.

The term 'alkylation' according to general process (B) includes the introduction of other groups such as cycloalkyl, alkenyl or phenalkyl groups.

Thus, for example, a compound of formula (I) in which X represents the group $NR^6$ and $R^6$ represents a $C_{1-6}$alkyl, $C_{3-7}$cycloalkyl, $C_{3-6}$alkenyl, $C_{3-10}$alkynyl, $C_{3-7}$cycloalkyl$C_{1-4}$alkyl or phenyl$C_{1-3}$alkyl group may be prepared by alkylating the corresponding compound of formula (I) in which $R^6$ represents a hydrogen atom, or a compound of formula (I) in which Im represents an imidazolyl group of formula (a) or (b) and $R^2$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^2$ represents a hydrogen atom, or a compound of formula (I) in which Q represents a $C_{1-4}$alkoxy group may be prepared by alkylating the corresponding compound in which Q represents a hydroxyl group.

The above alkylation reactions may be effected using conventional procedures, for example as described in published European patent specification No. 242973. Thus the reactions may be effected using an appropriate alkylating agent of formula $R^9G$ (where $R^9$ is the group to be introduced and G is a leaving atom or group), preferably in the presence of a base.

According to another embodiment of general process (B), a compound of formula (I) wherein X represents the group $NR^6$ and $R^6$ represents $-CO_2R^7$, $-COR^7$, $-CONR^7R^8$ or $-SO_2R^7$ may be prepared by acylating or sulphonylating as appropriate, a compound of formula (I) wherein $R^6$ represents a hydrogen atom. The acylation/sulphonylation reactions may be effected using an appropriate acylating/sulphonylating agent according to conventional procedures, for example, as described in published European patent specification No. 210840.

According to a yet further embodiment of general process (B), a compound of formula (I) in which Q represents a hydroxyl group may be prepared from the corresponding compound of formula (I) in which Q represents a $C_{1-4}$alkoxy or benzyloxy group, by acid-catalysed cleavage. The reaction may be effected using a Lewis acid such as boron tribromide or aluminium trichloride, in a solvent such as a halogenated hydrocarbon (e.g. dichloromethane). The reaction temperature may conveniently be in the range $-80°$ to $+100°$ C.

It should be appreciated that in the above transformations it may be necessary or desirable to protect any sensitive groups in the molecule of the compound in question to avoid undesirable side reactions. For example, when X represents the group NH and/or Im represents an imidazolyl group of formula (a) or (b), it may be necessary to protect the indole and/or imidazole nitrogen atoms respectively, for example with an arylmethyl (e.g. trityl), arylmethoxymethyl (e.g. phenylmethoxymethyl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. When Q represents a hydroxyl group it may be necessary to protect the hydroxyl group, for example with an arylmethyl (e.g. benzyl or trityl) group.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example, an arylmethoxymethyl N-protecting group may be cleaved by hydrogenolysis in the presence of a catalyst (e.g. palladium on charcoal). A trityl group may be cleaved by acid hydrolysis (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may be removed by alkaline hydrolysis. An arylmethyl OH-protecting group may be cleaved under acidic conditions (e.g. with dilute acetic acid, hydrobromic acid or boron tribromide) or by hydrogenolysis in the presence of a catalyst (e.g. palladium on charcoal).

Compounds of formula (II) may be prepared, for example, by a Beckmann rearrangement of an oxime of formula (IV):

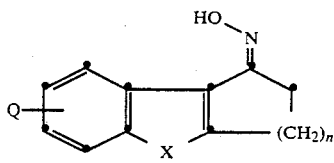

wherein X represents an oxygen or a sulphur atom or the group NR$^6$, or a protected derivative thereof. The Beckmann rearrangement may be effected using conventional methods, for example by using an acid (e.g. polyphosphoric or sulphuric acid, or a mixture of hydrochloric acid, acetic anhydride and acetic acid) optionally in the presence of an inert solvent such as an ether (e.g. dioxan), an amide (e.g. dimethylformamide) or a hydrocarbon (e.g. toluene or cyclohexane), at an elevated temperature of, for example, 50° to 120° C. Alternatively, the hydroxy group of the oxime of formula (IV), may be converted into a leaving atom or group such as a chloride, a hydrocarbylsulphonate (e.g. a mesylate or a tosylate) or a trifluoroacetate group. Subsequent heating at a temperature of, for example, 20° to 150° C., in an inert solvent as referred to above, gives a compound of formula (II).

Compounds of formula (IV) are either known, or may be prepared from the corresponding tricyclic ketone of formula (V):

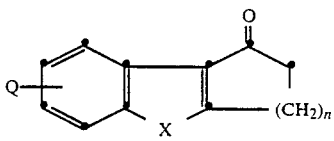

or a protected derivative thereof, using conventional methods, for example by using hydroxylamine hydrochloride in a solvent such as pyridine.

Compounds of formula (V) in which X represents an oxygen or a sulphur atom are either known compounds or may be prepared by the methods, or methods analogous to, those described by R. N. Castle et al., *J. Heterocycl. Chem.*, 1985, 22, 215. Compounds of formula (V) in which X represents the group NR$^6$ are either known compounds or may be prepared by the method or methods analogous to that described by H. Iida et al., *J. Org. Chem.*, 1980, 45, 2938. Compounds of formula (III) and protected derivatives thereof, are either known, or may be prepared, for example, by the methods or methods analogous to those described in German Offenlegungsschrift No. 3740352.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in ° C. Thin layer chromatography (t.l.c.) was carried out on silica, and flash column chromatography (FCC) and short-path column chromatography (SPCC) on silica (Merck 9385 and 7747 respectively). Solvent System A as used for chromatography denotes dichloromethane:ethanol:1:0.88 ammonia solution and System B denotes ethyl acetate: hexane. Organic extracts were dried, where indicated, over magnesium sulphate or sodium sulphate. The following abbreviations are used: DMF-dimethylformamide; THF - tetrahydrofuran.

INTERMEDIATE 1

2,3-Dihydro-1H-cyclopenta[b]benzofuran-1-one oxime

A mixture of 2,3-dihydro-1H-cyclopenta[b]benzofuran-1-one (1.0g) and hydroxylamine hydrochloride (1.21g), in dry pyridine was stirred at 60° under nitrogen for 24h. The solution was poured into 8% sodium bicarbonate solution (150ml) and extracted with dichloromethane (3×50 ml). The combined extracts were washed with water (2×10 0 ml), dried, and evaporated to give the title compound (1.1 g) as a foam, t.l.c. (System B, 1:2) Rf 0.46.

INTERMEDIATE 2

3,4-Dihydrobenzofuro[3,2-c]pyridin-1(2H)-one

A mixture of 2,3-dihydro-1H-cyclopent a[b]benzofuran-1-one oxime (1.0g) and polyphosphoric acid (ca.2 ml) was heated at 110° for 5h. Water (100 ml) was added and the suspension was extracted with ethyl acetate (3×50 ml). The combined extracts were dried and evaporated to give a solid (ca.325 mg) which was purified by FCC eluting with System B (1:1) to give the title compound, m.p. 158°–161°.

INTERMEDIATE 3

Benzo[b]thiophene-2-ethanamine

A solution of 2-(2-benzo[b]thiophene)ethanol (710 mg) in dry dichloromethane (30 ml) was cooled to −10°. Triethylamine (3 ml) was added, and stirring was continued for 10 min. under nitrogen. A solution of methanesulphonyl chloride (0.62 ml) in dry dichloromethane (8 ml) was added dropwise over 10 min. at −10°0 and stirring was continued at −10° for 2h and at room temperature for 10 min. The resultant suspension was washed with water (2×30 ml), dried, and evaporated to give an oil which was dissolved in dry DMF (15 ml) Potassium phthalimide (2.3 g) was added and the suspension was stirred at room temperature for 3 days under nitrogen. The suspension was then treated with water (50 ml), extracted with ethyl acetate (2×40 ml) and the combined, dried organic extracts were evaporated to give a solid (ca. 1.2 g) which was treated with ethanol (10 ml). 33% Ethanolic methylamine (4.5 ml) was added and the solution was stirred under nitrogen for 18h at room temperature. The mixture was evaporated and purified by FCC eluting with dichloromethane/ethanol (19:1) followed by System A (89:10:1) to give the title compound (325 mg) as an oil, t.l.c. (System A, 89:10:1) Rf 0.24.

INTERMEDIATE 4

Ethyl [2-(benzo[b]thiophen-2-yl)ethyl]carbamate

Ethyl chloroformate (0.18 ml) was added dropwise to a stirred, ice-cooled solution of benzo[b]thiophene-2-ethanamine (300 mg) in a mixture of chloroform (8 ml) and triethylamine (0.28 ml) under nitrogen and stirring was continued at 0° for 30 min. The solution was evaporated, the residue was treated with water (10 ml), extracted with dichloromethane (3×10 ml) and the combined, dried organic extracts were evaporated to give an oily solid. This was purified by FCC eluting with System B (1:2) to give the title compound (313 mg), m.p. 65°–66°.

INTERMEDIATE 5

3,4-Dihydro-[1]benzothieno[3,2-c]pyridin-1(2H)-one

A mixture of ethyl [2-(benzo[b]thiophen-2-yl)ethyl]-carbamate (285 mg), polyphosphoric acid (4 g) and phosphorus pentoxide (250 mg) was heated at 100°–110° for 6h. The cooled mixture was treated with water (25 ml) and the suspension was extracted with ethyl acetate (3×25 ml) The combined, dried organic extracts were purified by SPCC eluting with System B (1:1) to give the title compound (35 mg) as a solid, m.p. 143°–144°.

INTERMEDIATE 6

3,4-Dihydro-4-methylcyclopent[b]indol-1(2H)-one oxime 3,4-Dihydro-4-methylcyclopent[b]indol-1(2H)-one (1.7 g) and hydroxylamine hydrochloride (1.925 g) in pyridine were heated at 60° for 18h and cooled. The reaction mixture was evaporated in vacuo to a residue to which was added 8% sodium bicarbonate (150 ml). Extraction with ethyl acetate (300 ml) produced a suspension in the organic layer; this layer and associated solid was separated from the aqueous layer. The aqueous layer was re-extracted with ethyl acetate (250 ml). The combined organic extracts (and suspended solid) were evaporated to a residue, boiled with a mixture of ethanol (150 ml) and methanol (150 ml) and cooled to ca. 50°. The residue was adsorbed from this solution on to FCC silica and applied to an FCC column. Elution with ethyl acetate/3–10% methanol provided the title compound (1.69 g), m.p. 219°–224° (decomp.).

INTERMEDIATE 7

2,3,4,5-Tetrahydro-5-methyl-1H-pyrido[4,3-b]indol-1-one 3,4-Dihydro-4-methylcyclopent[b]indol-1(2H)-one oxime (1.53 g), polyphosphoric acid (40 g) and dioxan (15 ml) were heated at 110°–120° for 2.2h under nitrogen. The reaction mixture was cooled, and treated with 2N sodium carbonate solution ('l). The suspension was extracted with ethyl acetate (4×400 ml) and the combined extracts were dried. Evaporation gave a solid (1.43 g) which was recrystallised from ethyl acetate/cyclohexane. This solid was purified by FCC, eluting with System A (200:10:1) to give a solid (1.26 g) which was recrystallised from ethanol to provide the title compound (960 mg), m.p. 234°–238°.

INTERMEDIATE 8

1-(Chloromethyl)-2-methyl-1H-imidazole hydrochloride

Thionyl chloride (7.2 g) was added over 5 min to a stirred suspension of 1-(hydroxymethyl)-2-methyl-1H-imidazole (5.0 g) in a mixture of dichloromethane (50 ml) and DMF (0.5 ml) at 0°, and the mixture was stirred at 0° for 2h. It was then poured into dry ether (500 ml) and left for 1h. The cloudy supernatant was decanted from the insoluble colourless oil which separated. This oil was triturated with acetone (100 ml) with scratching to give a solid which was filtered off and dried to give the title compound (3.6 g), m.p. 122°–124°.

EXAMPLE 1

3,4-Dihydro-2-[(5-methyl-1H-imidazol-4-yl)methyl]-benzofuro[3,2-c]-pyridin-1(2H)-one maleate Sodium hydride (73% dispersion in oil; 20 mg) was added to a stirred solution of 3,4-dihydrobenzofuro[3,2-c]pyridin-1(2H)-one (95 mg) in dry dimethoxyethane (3 ml) under nitrogen. After 30 min. 4-(chloromethyl)-5-methyl-1-(triphenylmethyl)-1H-imidazole (227 mg) was added and the mixture was stirred at 50° for 18h. Acetic acid (1 ml) and water (1 ml) were added and the solution was heated at reflux for 1h. The mixture was poured into 8% sodium bicarbonate solution (30 ml) and extracted with dichloromethane (3×15 ml). The combined, dried organic extracts were evaporated to give a solid (ca.420 mg) which was purified by SPCC eluting with System A (200:10:1) to give the free base of the title compound (77 mg). This was dissolved in absolute ethanol (2 ml) and treated with a solution of maleic acid (33 mg) in absolute ethanol (1 ml). The solvent was removed in vacuo and the residue was triturated with dry ether (3×5 ml) to give the title compound (85mg), m.p. 285°–286°, t.l.c. (System A, 200:10:1) Rf 0.24.

EXAMPLE 2

3,4-Dihydro-2-[(5-methyl-1H-imidazol-4-yl)methyl]-[1]benzothieno[3,2-c]pyridin-1(2H)-one maleate A solution of 3,4-dihydro-[1]benzothieno[3,2-c]pyridin-1(2H)- one (152mg) in dry DMF (3ml) was added dropwise to a stirred, ice-cooled suspension of sodium hydride (78% dispersion in oil; 29mg) in dry DMF (1ml) under nitrogen and stirring was continued at room temperature for 1.5h. A suspension of 4-chloromethyl-5-methyl-1-(triphenylmethyl)-1H-imidazole (560mg) in dry THF (4ml) was added dropwise and stirring was continued at room temperature for 18h. A mixture of acetic acid (5ml), water (5ml) and THF (5ml) was added and the solution was heated at 100° for 1h, cooled, evaporated and treated with 8% aqueous sodium bicarbonate (35ml). The aqueous phase was extracted with ethyl acetate (2×25ml) and the combined, dried organic extracts were evaporated to give an oil. This was purified by SPCC eluting with System A (923:70:7) to give the free base of the title compound as a foam (32mg). This was further purified by FCC eluting with System A (89:10:1) to give an oil (20mg). This was dissolved in hot ethanol (3ml) and treated with a solution of maleic acid (8mg) in ethanol (1ml). The resultant solution was evaporated to give the title compound (25mg), m.p. 143°-145°, t.l.c. (System A, 89:10:1) Rf 0.27.

EXAMPLE 3

3,4-Dihydro-2-[(2-methyl-1H-imidazol-1-yl)methyl]-[1]benzothieno[3,2-c]pyridin-1(2H)-one maleate A mixture of 3,4-dihydro-[1]benzothieno[3,2-c]pyridin-1(2H)-one (1.0g) in dry dimethoxyethane (50ml) was treated with sodium hydride (73% dispersion in oil; 543mg) and the suspension was stirred at 60° for 4h under nitrogen. 1-(Chloromethyl)-2-methyl-1H-imidazole hydrochloride (1.3g) was added in portions, and the mixture was stirred for 18h. The mixture was poured into water and extracted with dichloromethane (3×100ml). The combined organic extracts were washed with brine (2×100ml), evaporated in vacuo and the residue was purified by FCC eluting with System A (200:8:1) to give the free base of the title compound as a solid (0.1g). A solution of this solid in methanol (5ml) was treated with maleic acid (39mg) and heated on a steam bath for 15 min. The solution was cooled to 21° and treated with ether (15ml) to give the title compound (120mg) as a solid, m.p. 144°-145°.

Analysis Found: C,58.2; H,4.6; N,9.8; $C_{16}H_{15}N_3OS \cdot C_4H_4O_4$ requires C,58.1; H,4.6; N,10.2%.

EXAMPLE 4

2,3,4,5-Tetrahydro-5-methyl-2-[(2-methyl-1H-imidazol-1yl)methyl]-1H-pyrido[4,3-b]indol-1-one maleate A mixture of 2,3,4,5-tetrahydro-5-methyl-1H-pyrido[4,3-b]indol-1-one (0.6g) and sodium hydride (ca. 73% dispersion in oil; 0.3g) in dry DMF (15ml) under nitrogen was stirred at 40° for 0.5h, and was then treated with 1-(chloromethyl)-2-methyl-1H-imidazole hydrochloride (1.0g) at 40° for 3h. The mixture was partitioned between saturated potassium carbonate solution (100ml) and ethyl acetate (3×50ml). The combined organic extracts were washed with brine (2×90ml), dried, and evaporated in vacuo to leave a semi-solid (ca. 1.0g) which was purified by SPCC eluting with System A (200:8:1) to give a solid (0.4g). This solid was further purified by SPCC eluting with System A (200:8:1) to give the free base of the title compound (0.063g). This was dissolved in ethanol (5ml) and treated with maleic acid (22mg) in ethanol (1ml). The resulting solution was concentrated to ca. 3ml to precipitate the title compound (71mg) as a solid, m.p. 153°-155°.

Analysis Found: C,61.3; H,5.4; N,13.6; $C_{17}H_{18}N_4O \cdot C_4H_4O_4$ requires C,61.5; H,5.4; N,13.6%.

A further crop of the free base of the title compound (0.1 g) was obtained from the second SPCC purification. This was treated with maleic acid (49 mg) in ethanol (5 ml) to precipitate the title compound (102 mg) as a solid, m.p. 152°-153°, analysis consistent with that required for $C_{17}H_{18}N_4O \cdot C_4H_4O_4$.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

| Direct Compression Tablet | | |
|---|---|---|
| | mg/tablet | |
| Active Ingredient | 0.50 | 10.00 |
| Calcium Hydrogen Phosphate BP* | 87.25 | 77.75 |
| Croscarmellose Sodium NF | 1.80 | 1.80 |
| Magnesium Stearate BP | 0.45 | 0.45 |
| Compression weight | 90.00 | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| INJECTION FOR INTRAVENOUS ADMINISTRATION | | |
|---|---|---|
| | mg/ml | |
| Active ingredient | 0.05 | 1.0 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:
1. A compound of formula (I)

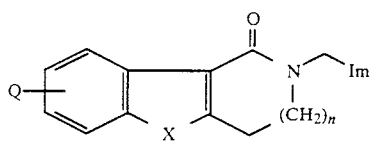

wherein Im represents an imidazolyl group of the formula (a), (b) or (c):

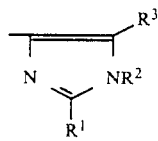

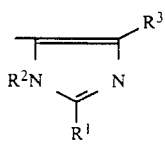

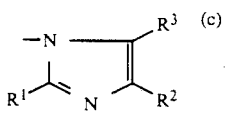

one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group; n represents 1 or 2;

Q represents a hydrogen atom, a halogen atom, or a hydroxy, $C_{1-4}$alkoxy, phenyl$C_{1-3}$alkoxy or $C_{1-6}$alkyl group, or a group —$NR^4R^5$ or —$CONR^4R^5$ (wherein $R^4$ and $R^5$, which may be the same or different, each represents a hydrogen atom or a $C_{1-4}$alkyl or $C_{3-4}$alkenyl group, or together with the nitrogen atom to which they are attached from a saturated 5 to 7 membered ring); and X represents an oxygen or a sulphur atom, and, when Im represents an imidazolyl group of formula (c), X may also represent the group $NR^6$, where $R^6$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, —$CO_2R^7$, —$COR^7$, —$CONR^7R^8$ or —$SO_2R^7$ (where $R^7$ and $R^8$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^7$ does not represent a hydrogen atoms when $R^6$ represents a group —$CO_2R^7$ or —$SO_2R^7$); or a physiologically acceptable salt or solvate thereof.

2. A compound according to claim 1 in which $R^1$, $R^2$ and $R^3$ each independently represent a hydrogen atom or a $C_{1-6}$alkyl group.

3. A compound according to claim 1 in which Im represents an imidazolyl group of formula (a) or (b).

4. A compound according to claim 3 in which $R^1$ and $R^2$ each represent a hydrogen atom and $R^3$ represents a $C_{1-3}$alkyl group.

5. A compound according to claim 2 in which Im represents an imidazolyl group of formula (c), $R^1$ represents a $C_{1-3}$alkyl group and $R^2$ and $R^3$ each represent hydrogen atoms.

6. A compound according to claim 1 in which n represents 1.

7. A compound according to claim 1 in which Q represents a hydrogen atom.

8. A compound according to claim 1 in which $R^1$, $R^2$ and $R^3$ each represents a hydrogen atom or a $C_{1-3}$alkyl group, n represents 1, Q represents a hydrogen atom and X represents an oxygen or sulphur atom or the group $NR^6$ where $R^6$ represents a $C_{1-3}$alkyl group.

9. A compound selected from
3,4-dihydro-2-[(5-methyl-1H-imidazol-4-yl)methyl]-benzofuro[3,2-c]pyridin-1(2H)-one;
3,4-dihydro-2-[(5-methyl-1H-imidazol-4-yl)methyl][1-]benzothieno-[3,2-c]pyridin-1(2H)-one;
or a physiologically acceptable salt or solvate thereof.

10. A pharmaceutical composition for treating a condition mediated through 5-$HT_3$ receptors which comprises an effective amount to relieve said condition of at least one compound of formula (I) as defined in claim 1 or a physiologically acceptable salt or solvate thereof together with at least one physiologically acceptable carrier or excipient.

11. A method of treating a condition mediated through 5-$HT_3$ receptors which comprises administering to a patient an effective amount to relieve said condition of a compound of formula (I) as defined in claim 1 or a physiologically acceptable salt or solvate thereof.

* * * * *